(12) United States Patent
Havens et al.

(10) Patent No.: US 7,749,768 B2
(45) Date of Patent: Jul. 6, 2010

(54) NON-INVASIVE METHOD OF DETERMINING OXYGEN CONCENTRATION IN A SEALED PACKAGE

(75) Inventors: Marvin Russell Havens, Greer, SC (US); Charles Rice Barmore, Moore, SC (US)

(73) Assignee: Cryovac, Inc., Duncan, SC (US)

( * ) Notice: Subject to any disclaimer, the term of this patent is extended or adjusted under 35 U.S.C. 154(b) by 1150 days.

(21) Appl. No.: 11/375,711

(22) Filed: Mar. 13, 2006

(65) Prior Publication Data

US 2007/0212789 A1    Sep. 13, 2007

(51) Int. Cl.
*G01N 21/76* (2006.01)
*G01N 21/64* (2006.01)
*G01N 33/00* (2006.01)
*G01N 7/00* (2006.01)

(52) U.S. Cl. .............. 436/172; 436/127; 436/164; 422/55; 422/82.05; 422/82.07; 422/82.08; 422/82.11; 42/83; 42/84; 42/85; 42/86

(58) Field of Classification Search .............. None
See application file for complete search history.

(56) References Cited

U.S. PATENT DOCUMENTS

| | | |
|---|---|---|
| 4,285,697 A | 8/1981 | Neary |
| 4,526,752 A | 7/1985 | Perlman et al. |
| 4,772,560 A | 9/1988 | Attar |
| 4,810,655 A | 3/1989 | Khalil et al. |
| 4,820,606 A | 4/1989 | Miyasaka et al. |
| 4,857,472 A | 8/1989 | Wolfbeis |
| 5,043,286 A | 8/1991 | Khalil et al. |
| 5,047,350 A | 9/1991 | Switalski et al. |
| 5,057,277 A | 10/1991 | Mauze et al. |

(Continued)

FOREIGN PATENT DOCUMENTS

DE            197 19 422 A1    11/1998

(Continued)

OTHER PUBLICATIONS

Lakowicz, *The Principles of Fluorescence Spectroscopy—Second Edition*, pp. 4-6, 10-11, and 237-265, 1999.

(Continued)

*Primary Examiner*—Jill Warden
*Assistant Examiner*—Neil Turk
(74) *Attorney, Agent, or Firm*—Alston & Bird LLP

(57) ABSTRACT

The invention is a method of measuring oxygen concentration in a package having an oxygen sensitive product disposed therein. The method includes exposing a luminescent compound that is disposed in an interior of the package to light having a wavelength that is absorbed by the luminescent compound so that the luminescent compound is promoted into an excited state. When the exposure of the light is terminated, the excited luminescent compound emits light that is detectable by a detector positioned outside of the package. The intensity of the emitted light is inversely proportional to the oxygen concentration and is used in conjunction with mathematical function that describes the luminescent intensity of the luminescent compound as a function of oxygen concentration and temperature to calculate the oxygen concentration. The method may be used to verify and track the oxygen concentration of a package as it moves through a distribution system.

14 Claims, 4 Drawing Sheets

U.S. PATENT DOCUMENTS

| | | |
|---|---|---|
| 5,096,813 A | 3/1992 | Krumhar et al. |
| 5,108,932 A | 4/1992 | Wolfbeis |
| 5,114,676 A | 5/1992 | Leiner et al. |
| 5,242,835 A | 9/1993 | Jensen |
| 5,316,949 A | 5/1994 | Bull et al. |
| 5,403,746 A | 4/1995 | Bentsen et al. |
| 5,409,666 A | 4/1995 | Nagel et al. |
| 5,439,648 A | 8/1995 | Balderson et al. |
| 5,458,896 A | 10/1995 | Porter |
| 5,483,819 A | 1/1996 | Barmore et al. |
| 5,495,850 A | 3/1996 | Zuckerman |
| 5,515,864 A | 5/1996 | Zuckerman |
| 5,583,047 A | 12/1996 | Blinka et al. |
| 5,617,812 A | 4/1997 | Balderson et al. |
| 5,863,460 A | 1/1999 | Slovacek et al. |
| 5,958,782 A | 9/1999 | Bentsen et al. |
| 6,009,339 A | 12/1999 | Bentsen et al. |
| 6,015,715 A | 1/2000 | Kirschner et al. |
| 6,190,612 B1 | 2/2001 | Berger et al. |
| 6,297,508 B1 | 10/2001 | Barmore et al. |
| 6,325,978 B1 | 12/2001 | Labuda et al. |
| 6,664,111 B2 | 12/2003 | Bentsen et al. |
| 6,914,677 B2 | 7/2005 | Mader et al. |
| 2003/0008400 A1 | 1/2003 | Putnam et al. |
| 2003/0143118 A1 | 7/2003 | Draaijer |
| 2003/0190262 A1 | 10/2003 | Blazewicz et al. |
| 2004/0086749 A1 | 5/2004 | Kennedy et al. |
| 2004/0131806 A1 | 7/2004 | Barmore et al. |
| 2004/0171094 A1 | 9/2004 | Klimant et al. |
| 2004/0185154 A1 | 9/2004 | Garwood |
| 2006/0171845 A1 | 8/2006 | Martin et al. |

FOREIGN PATENT DOCUMENTS

| | | |
|---|---|---|
| EP | 0 252 578 A2 | 1/1988 |
| EP | 0 524 021 | 9/1997 |
| GB | 2 132 348 | 5/1987 |
| JP | 2003307513 | 10/2003 |
| WO | WO 87/00023 AI | 1/1987 |
| WO | WO 01/63264 | 8/2001 |
| WO | WO 01/69243 | 9/2001 |
| WO | WO 02/099416 | 12/2002 |
| WO | WO 2004/052644 A | 6/2004 |
| WO | WO 2005/059500 A1 | 6/2005 |

OTHER PUBLICATIONS

Carraway et al., "Photophysics and Photochemistry of Oxygen Sensors Based on Luminescent Transition-Metal Complexes," *Analytical Chemistry*, vol. 63, No. 4, Feb. 15, 1991, pp. 337-342.

Draxler et al., "Effects of Polymer Matrices on the Time-Resolved Luminescence of a Ruthenium Complex Quenched by Oxygen," *J. Phys. Chem.*, vol. 99, No. 10, 1999, pp. 3162-3167.

Colvin, Jr., et al., "A Novel Solid-State Oxygen Sensor," *Johns Hopkins APL Technical Digest*, vol. 17, No. 4, 1996, pp. 377-385.

Debye, *Physikalische Zeitschrift*, XX, 1919, pp. 183-188.

Atkinson, "Monitoring—Non-Invasive Method for Determining Oxygen in Food Packaging," *Food, Cosmetics and Drug Packaging*, Jun. 2000, 2 pages.

Bacon et al., "Determination of Oxygen Concentrations by Luminescence Quenching of a Polymer-Immobilized TransitionComplex," *Analytical Chemistry*, vol. 59, No. 23, Dec. 1, 1987, pp. 2780-2785.

$O_2$xySense™ 4000B—Portable Oxygen Analyzer (3 pages) available at www.oxysense.com/4000.htm; www.oxysense.com/4000_2.1htm; www.oxysense.com/4000_3.htm; and www.oxysense.com/4000_4.htm.

OxySense—How it Works (6 pages) available at www.oxysense.com/how_it_works.htm; www.oxysense.com/how_it_works2.htm; www.oxysense.com/how_it_works3.htm; www.oxysense.com/how_it_works4.htm; www.oxysense.com/how_it_works5.htm; www.oxysense.com/how_it_works6.htm.

$O_2$xyDot™—R&D and Development Sensor (3 pages) available at www.oxysense.com/oxydot.htm; www.oxysense.com/oxydot_2.htm; www.oxysense.com/oxydot_3.htm.

Fresnel Lens (1 page) available at www.hyperphysics.phy-astr.gsu.edu/hbase/geoopt/fresnellens.html.

Whatis.com—Solid State (2 pages) available at www.whatis.techtarget.com/definition/0,,sid9_gci500174,00.html.

Hannemann, B. et al., *The Influence of Temperature of the Luminescence Decay Time on the Behaviour of a Luminescence Quenching Oxygen Sensor*, SPIE, vol. 2388, 1995, pp. 385-388.

Lam, S. K. et al., *Characterization of Phosphorescence Oxygen Sensor Based on Erythrosin B in Sol-Gel Silica in Wide Pressure and Temperature Ranges*, Sensors and Actuators B, Elsevier Sequoia S.A., vol. 73, No. 2-3, 2001, pp. 135-141.

Ogurtsov, V. I. et al., *Modelling of Phase-Fluorometric Oxygen Sensors: Consideration of Temperature Effects and Operational Requirements*, Sensors and Actuators B, Elsevier Sequoia S.A., vol. 113, No. 2, 2006, pp. 917-929.

Search Report for PCT/US2007/063809 dated Aug. 17, 2007.

Search Report for PCT/US2007/063804 dated Aug. 17, 2007.

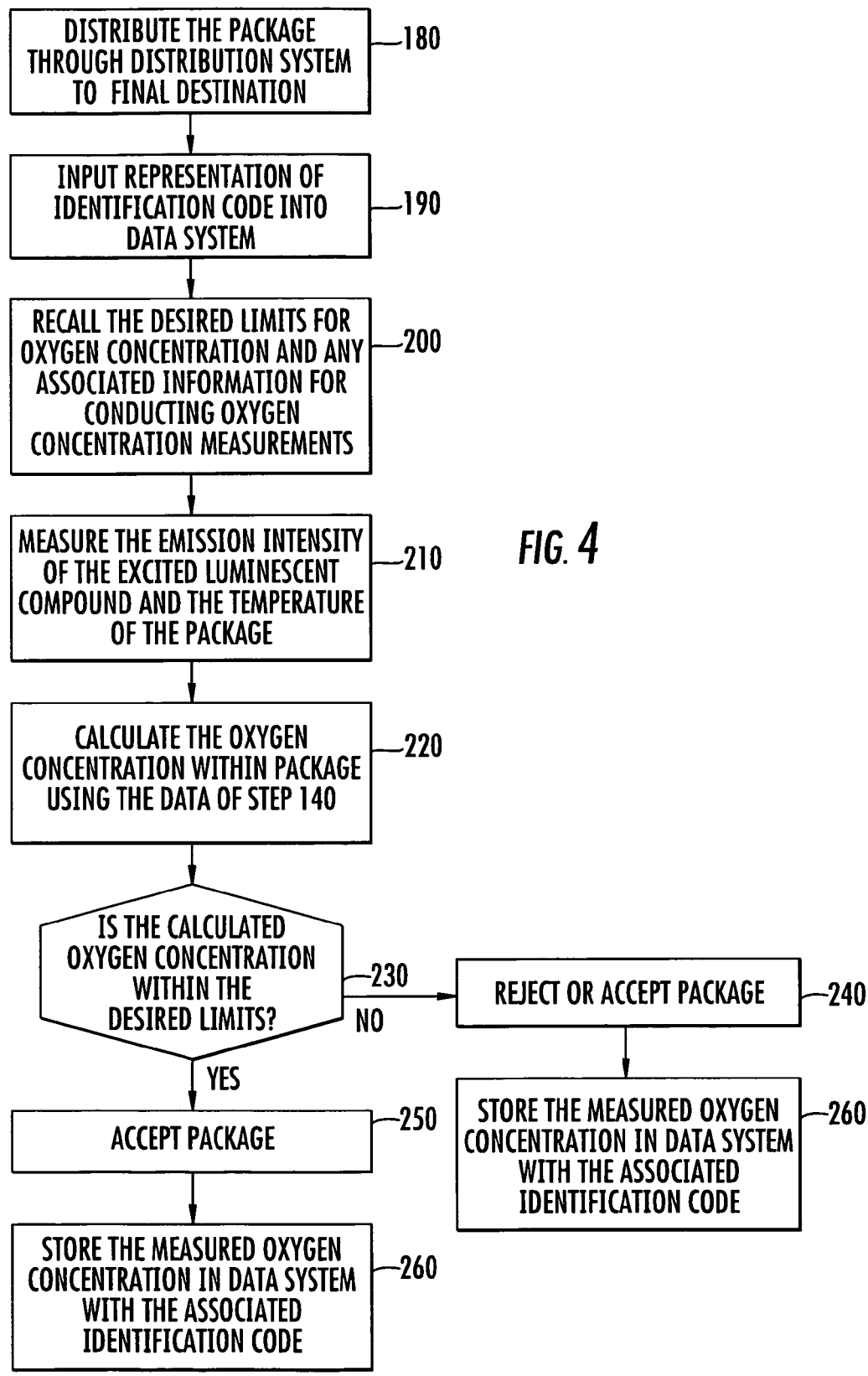

NON-INVASIVE METHOD OF DETERMINING OXYGEN CONCENTRATION IN A SEALED PACKAGE

FIELD OF THE INVENTION

The invention relates generally to oxygen concentration measurements and more particularly to measuring the concentration of oxygen is a sealed package using an oxygen sensitive luminescent compound.

BACKGROUND OF THE INVENTION

It is generally known that reducing the exposure to oxygen of oxygen sensitive articles maintains and enhances the quality and shelf life of the article. For instance, reducing the oxygen exposure of oxygen sensitive food products in a packaging system maintains the quality of the food product and avoids food spoilage. Foods, beverages, pharmaceuticals, medical devices, corrodible metals, analytical chemicals, electronic devices, and many other products may perish or experience diminished shelf life when stored too long in the presence of oxygen. Reduced oxygen exposure may help keep the product in inventory longer, thereby reducing costs incurred from waste and having to restock.

Manufacturers of packaging materials have developed packaging materials and systems to limit the amount of oxygen to which a packaged article may be exposed. Such materials and methods may include packaging articles in a package environment, or "headspace", with reduced oxygen levels. Modified Atmosphere Packaging (MAP) and vacuum packaging are two methods that are commonly used to limit the amount of oxygen in a package. MAP involves the modification of the headspace gas in a package in order to prolong the shelf life of the product it contains. In some MAP applications, the head space may have substantially no oxygen. In other MAP applications, the headspace may have a predetermined level of oxygen. The success of MAP generally depends on the ability to control the concentration of oxygen within the package. In vacuum packaging, the atmosphere may be substantially removed so that the package environment is substantially free of oxygen.

In MAP applications for meat products, the raw meat may be packaged in a low level oxygen ($O_2$) environment. Packaging systems having low levels of oxygen are desirable because the fresh quality of meat can generally be preserved longer under anaerobic conditions than under aerobic conditions. Maintaining low levels of oxygen minimizes the growth and multiplication of aerobic bacteria. One example of a modified atmosphere environment is a mixture of gases consisting of about 30 percent carbon dioxide ($CO_2$) and about 70 percent nitrogen ($N_2$). Typically, low oxygen packaging environments may provide an atmosphere that helps prevent or inhibit excessive metmyoglobin (brown) formation in red meat products. In some MAP applications, it may be desirable to maintain the oxygen level at a predetermined concentration.

Another method of reducing oxygen exposure is to incorporate an oxygen scavenging composition into the packaging structure, such as in a film or tray. Oxygen scavenging compositions are compositions that consume, deplete, or reduce the amount of oxygen in a given environment. There are a wide variety of different compositions that can be used in oxygen scavenging applications. Exemplary compositions are described in U.S. Pat. Nos. 5,211,875; 5,350,622; 5,399,289; and 5,811,027 to Speer et al. and WO 99/48963 to Cai et al. The oxygen scavenging compositions can be "triggered" by exposing the composition to a radiation source, such as actinic radiation, having sufficient power for a sufficient amount of time to initiate oxygen scavenging.

Methods of triggering oxygen scavenging compositions typically use low-pressure mercury germicidal lamps that have an intensity output from about 5 to 10 $mW/cm^2$. These lamps are commonly referred to as germicidal since the principal emission is at 254 nm. A dosage of UV-C light between about 100 to 1600 $mJ/cm^2$ is typically needed to trigger oxygen scavenging. For details on preferred methods for activating such oxygen scavenging compositions at point of use, see Speer et al., U.S. Pat. No. 5,211,875, Becraft et al., U.S. Pat. Nos. 5,911,910, and 5,904,960, and co-pending applications U.S. Ser. No. 09/230,594 filed Aug. 1, 1997, and Ser. No. 09/230,776 filed Jul. 29, 1997, and U.S. Pat. No. 6,233,907 (Cook et al.), all of which are incorporated herein by reference in their entirety.

Unfortunately, oxygen scavengers do not always activate on command. This may result from a number of factors, including defective scavenger compositions, inadequate triggering conditions, operator error, or a combination of these or other factors. In many instances, it may not be readily apparent whether the oxygen scavenging composition is defective or whether the failure originated in the triggering equipment. Typically, conventional oxygen scavengers do not themselves visually indicate whether or not they are active. In response to this uncertainty, operators of packaging assembly plants prefer to verify scavenger activity as soon as possible after triggering. The longer a failed triggering attempt remains undiscovered, the more waste and expense is incurred, especially where packaging equipment operates at high speeds.

In addition, defective seals or openings in the packaging may permit oxygen to enter into the headspace within a package. Such defective packaging may not be easily discernable. As a result, a packaged article may be exposed to an undesirable level of oxygen, which may result in loss of shelf-life or spoilage.

There are several methods for verifying oxygen concentration in a package. Prior art methods for verifying oxygen scavenger activity in a low oxygen package involve detecting oxygen concentrations in the package headspace. Oxygen concentrations are typically measured after the package has been assembled and equilibrium of oxygen levels established among the headspace, package layers, and package contents. Detection of sufficiently reduced oxygen levels within the headspace allows one to determine if the package has maintained a low oxygen atmosphere and to infer whether an oxygen scavenging compound has been successfully activated.

Under this approach, one typically has two options, neither of which is particularly satisfactory. One option is to leave an oxygen indicator in the package headspace after it has been assembled and sealed. For example, Mitsubishi teaches an indicator comprising glucose and methylene blue, encased within a sachet. The sachet is left inside the package after it is sealed. A color change within the sachet indicates the presence of unwanted oxygen.

This approach has several disadvantages, however. Sachets must be attached to the package to avoid their being accidentally ingested by the consumer. Some package contents require a moisture-free storage environment. Yet, in the case of the Mitsubishi glucose/methylene blue indicator, moisture may be required to produce a color change. Also, sachets potentially introduce contaminants or other substances into the package that may be incompatible with its contents or accidentally ingested. For some applications, manufacturers may not want to leave indicators in packages where consumers may misinterpret the information the indicator provides.

Another option is to use probes to measure the gas content within the headspace. One commonly used headspace gas analyzer is available from Mocon Inc. Unfortunately, probes that rely on gas chromatography and other such analytical techniques cannot measure oxygen concentration in vacuum packages, where there is substantially no atmosphere to measure. In all cases, probes require sacrificing the sampled package. This technique invariably requires some sort of device that will penetrate the package and remove a portion of the gas within the headspace. The device inevitably leaves a hole in the package, destroying the integrity of the package.

Thus, there exists a need for a non-invasive method of measuring oxygen concentration in a sealed package.

BRIEF SUMMARY OF THE INVENTION

The invention provides a method of measuring the oxygen concentration in a package having an oxygen sensitive product disposed in an interior space of the package. In one embodiment, the method comprises exposing a luminescent compound that is disposed in an interior of the package to light having a wavelength that is strongly absorbed by the luminescent compound so that the luminescent compound is promoted into an excited state. When the exposure of the light is terminated, the excited luminescent compound may emit light that is detectable by a detector positioned outside of the package. The intensity of the emitted light is inversely proportional to the oxygen concentration. As a result, the internal oxygen concentration within the package may be measured by calculating the intensity of the emitted light.

In one embodiment, the emission of excited light as a function of time produces an exponential decay curve, the area of which is tau. Applicants have discovered that the oxygen concentration can be determined over a wide temperature range by applying a mathematical function that that describes the luminescent intensity of the luminescent compound as a function of oxygen concentration and temperature. In one embodiment, the oxygen concentration may be calculated with the following equation:

$$[O_2]=(A_{Ta}(T)^2+B_{Ta}(T)+C_{Ta})(\text{tau})^2+(A_{Tb}(T)^2+B_{Tb}(T)+C_{Tb})(\text{tau})+(A_{Tc}(T)^2+B_{Tc}(T)+C_{Tc})$$

wherein:

T is the measured temperature;

tau is the coefficient of the exponential decay curve; and $A_{Ta}$, $B_{Ta}$, $C_{Ta}$, $A_{Tb}$, $B_{Tb}$, $C_{Tb}$, $A_{Tc}$, $B_{Tc}$, and $C_{Tc}$ are previously determined coefficients for the luminescent compound that describes the luminescent intensity of the luminescent compound as a function of oxygen concentration and temperature. The measured temperature may be indicative of the temperature of the luminescent compound, and hence, any oxygen contained within the package.

The Applicants have also discovered that limiting heat from the surrounding environment and from the electronics of the apparatus that is used to measure the temperature may help improve the accuracy of the calculated oxygen concentration. To help improve the accuracy of the temperature measurement the method may include contacting an exterior surface of the package with a temperature sensor. In some embodiments, the temperature sensor may be thermally isolated from the surrounding environment.

In one embodiment, the invention is directed to a method of verifying and tracking the oxygen concentration of the package before it is shipped or distributed. In another embodiment, the oxygen concentration may be verified at various locations as the package moves through a distribution system. Measuring the oxygen concentration of the package may help improve the quality of products being distributed and may also help prevent products that may have a higher likelihood of spoilage from reaching a consumer. In addition, it may permit oxygen sensitive packages to be repackaged if the measurements indicate that the oxygen concentration within the package may be too high or too low. As a result, the method may help reduce costs that may be associated with wasted product.

In some embodiments, the invention comprises associating information relating to the package with an identification code in a data system. The identification code may then be used to recall the information. In one embodiment, the package may include a representation of the identification code, such as a bar code, that is attached to the package. The identification code may be inputted into the data system by scanning the representation of the identification code with a data entry device, such as a bar code scanner. The information associated with the identification code may then be recalled. The identification code may be unique to the package. In one embodiment, the measured oxygen concentration may be recalled by scanning the representation of the identification code into the data system. In another embodiment, the measured oxygen concentrations can also be associated with the identification code in the data system. As a result, the measured oxygen concentrations for the package may be recalled and viewed to determine a history of the package. Tracking the oxygen concentration of the package as it moves through the distribution system may help a packager/supplier determine the location of any problems within the packaging or distribution system. As stated above, it may also provide assurance of the quality of the product.

In another embodiment, the method of verifying and tracking oxygen concentration within a sealed package may be particularly advantageous in the food packaging industry. Many food products are oxygen sensitive and may have a shorter shelf-life when exposed to oxygen. Measuring and tracking the oxygen concentration of the package may help verify that the packages have a low oxygen atmosphere when they leave the packaging facility and have maintained the low oxygen atmosphere throughout the distribution system. Measuring the oxygen exposure may also permit the oxygen measurement history of a package to be recalled and examined. Based on the oxygen measurements associated with the package, one can make a determination as to the likelihood of spoilage of the packaged product. If the oxygen measurements indicate that the failure of the packaging occurred relatively recently, the shelf-life of the product may not be significantly affected. In such a case, the product may be sold at regular or a discounted price. On the other hand, the package may be rejected or disposed of if the history indicates that the failure may have occurred at a time that may adversely affect the shelf-life.

Thus, the invention provides a non-invasive method of measuring oxygen concentration within a sealed package that may be used to verify and track the package's oxygen concentration.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 4 is a block diagram depicting a method of measuring temperature at a point along the distribution system.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

In one embodiment, the invention is directed to a method for measuring oxygen concentration within a sealed package. A method of measuring the oxygen concentration within the sealed package may include exciting a luminescent compound that is disposed in an interior of the package and then measuring the resulting luminescent intensity as a function of time. The intensity of the luminescent emission is inversely proportional to the oxygen concentration within the sealed package. The luminescent intensity may be used to calculate the oxygen concentration within the package. As a result, the oxygen concentration of the package can be measured without piercing the package exterior or having to remove a sample of the atmosphere within the sealed package.

The term "package" as used herein shall be defined as any means for holding an oxygen sensitive product, such as raw meat, including a container, carton, casing parcel, holder, tray, flat, bag, pouch, film, case-ready packaging, envelope, bottle, etc. A wide variety of package types may be used in the practice of the invention. In one embodiment, the package comprises a thermoplastic material that may be used in vacuum packaging applications. In another embodiment, the package may comprise a thermoplastic bag having an opening into which an item may be inserted. The opening of the package may be sealed after the item has been inserted into the package. In other embodiments, the package may comprise foamed trays including case-ready packaging, cartons, boxes, and the like. In one embodiment, the invention may be used to measure the oxygen concentration of a sealed package having a food product, such as a meat product, disposed therein.

Figure 1:
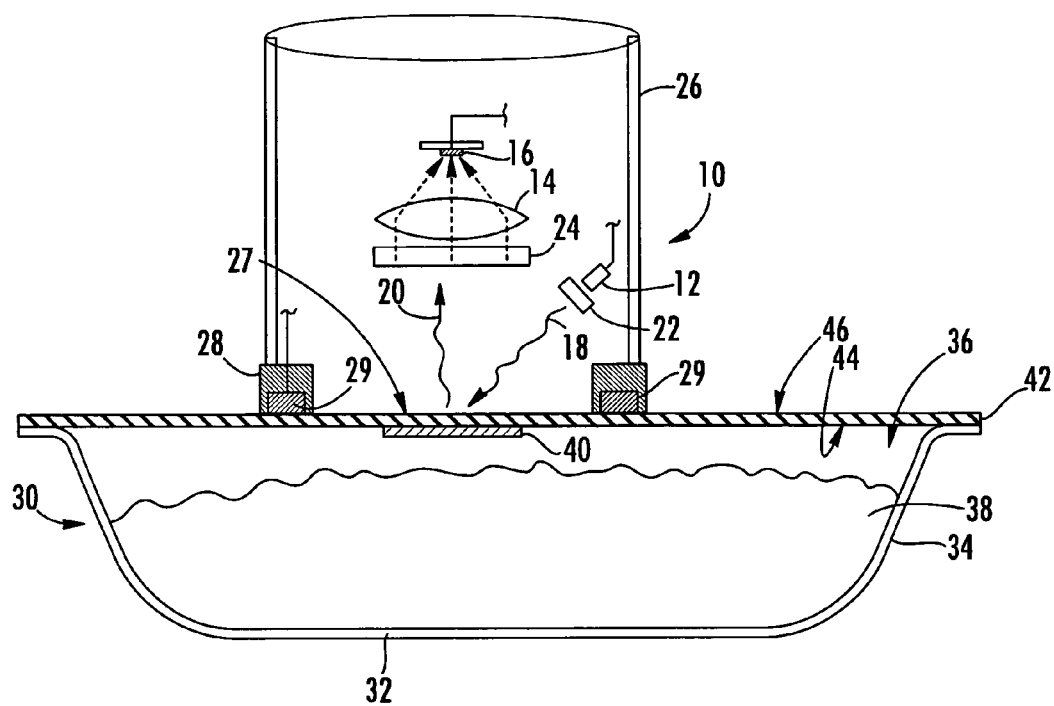
FIG. 1 is a cross-sectional side view depicting an apparatus for measuring the oxygen concentration within a sealed package and wherein the apparatus is positioned in a oxygen-measuring relationship with the package.

With reference to FIG. 1, a schematic illustration of an exemplary apparatus for measuring the concentration in a sealed package is illustrated and broadly designated as reference number 10. In one embodiment, the sealed package 30 comprises a support member 32 having sidewalls 34 defining an interior space or cavity 36 in which an oxygen sensitive product, such as a food product 38 may be disposed, and a luminescent compound 40 disposed in an oxygen-quenching relationship with the interior of the package 36. In one embodiment, a lidstock 42 such as a film may enclose the product 38 and the luminescent compound within the package. The luminescent compound is depicted as being attached to an inner surface 44 of the lidstock.

In one embodiment, the package 30 may comprise a vacuum sealed package or a modified atmosphere package having a low or high oxygen concentration. To maintain the desired atmosphere within the package, the lidstock and the support member may have barrier properties that substantially prevent the ingress or egress of oxygen in and out of the package. In one embodiment, the package includes an oxygen sensitive product such as a food product, beverage, pharmaceutical, medical device, corrodible metal, analytical chemical, electronic device, and any other product that may perish or experience diminished shelf life when stored too long in the presence of oxygen.

As shown, the apparatus 10 is positioned in an oxygen-measuring relationship with a luminescent compound 40 that is disposed in an interior space of the sealed package. In the context of the invention, an "oxygen-measuring relationship" refers to a position of the apparatus with respect to the package wherein excitation light from the apparatus is capable of reaching and exciting the luminescent compound and where luminescent light emitted by the compound is able to be detected by a detector.

The apparatus 10 may include an excitation source 12, focusing optics 14, and a detector 16. In operation, excitation light source 12 emits light 18 having a wavelength that excites the luminescent compound 40. As the excited luminescent compound relaxes to the ground state it may emit light 20 that is detectable by detector 16. Light emitted by the luminescent compound is referred to as "luminescent light." In the presence of oxygen, the intensity of such an emission is reduced based on the oxygen concentration in the container. In one embodiment, the detector 16 produces an electronic signal in response to luminescent light impacting the detector. The electronic signal may then be communicated to a control unit (not shown), such as a processor, that is configured to analyze the intensity data and calculate the oxygen concentration within the container. The apparatus may also include filters 22, 24 that may filter out certain undesirable wavelengths of light.

In one embodiment, the apparatus 10 may comprise a handheld device having a housing 26 that may be configured to be portable and easily supported by an operator. The housing 26 may comprise a material that is lightweight and strong, such as a thermoplastic material. As shown, the various components and instrumentation for exciting the luminescent compound and collecting the luminescent emissions may be disposed within housing 26. In one embodiment, the housing 26 has a generally cylindrical shape. The cylindrical shape may permit an operator to easily grip and manipulate the apparatus.

The housing 26 may include an opening 27 defining an aperture through which excitation light generated by the excitation source 12 exits the housing and luminescent light enters the housing. The size of the opening may be configured so that a substantial portion of light emitted by the luminescent compound enters into an interior of the apparatus and is collected via focusing optics 14. The use of a relatively large aperture and focusing optics may increase the amount of light that the apparatus is able to collect and thereby improve the sensitivity of the apparatus. Additionally, the use of a relatively large aperture may permit some leeway in the positioning of the apparatus with respect to the luminescent compound. As a result, an operator may be able to quickly position the apparatus in an oxygen-measuring relationship with luminescent compound without having to find an exact position for the apparatus. An exemplary apparatus for measuring oxygen concentration in a sealed package is discussed in commonly owned U.S. patent application Ser. No. 11/375,557 entitled METHOD AND APPARATUS FOR MEASURING THE OXYGEN CONCENTRATION WITHIN A CONTAINER to Havens et al., filed Mar. 13, 2006, the contents of which are hereby incorporated by reference.

Generally, the luminescence of the excited luminescent follows an exponential decay curve as the excited compound relaxes to the ground state. The exponential coefficient of the decay curve is known as τ (tau). The value of tau is inversely proportional to the oxygen concentration and may be determined by calculating the area of the exponential decay curve. Temperature also affects the luminescent intensity and the value of tau because oxygen quenching is a diffusion controlled process. At higher temperatures, the diffusion rate of oxygen increases which results in a greater amount of collisional quenching, and hence lower intensities and smaller tau values. Conversely, at lower temperatures the diffusion rate of oxygen is decreased which results in relatively higher emission intensities and greater tau values.

Many oxygen sensitive goods are also temperature sensitive. For example, fresh meat products are typically packaged and stored under refrigerated conditions to prolong the shelf-life of the product. The temperatures at which oxygen sensitive products are maintained may vary widely from product to product. Accordingly, it is important to account for temperature when using luminescent compounds to measure the oxygen concentration within a package. Applicants have discovered that the oxygen concentration can be determined over a wide temperature range by applying a mathematical function that that describes the luminescent intensity of the luminescent compound as a function of oxygen concentration and temperature. For example, Applicants have discovered that following equation for calculating oxygen concentration:

$$[O_2] = (A_{Ta}(T)^2 + B_{Ta}(T) + C_{Ta})(\text{tau})^2 + (A_{Tb}(T)^2 + B_{Tb}(T) + C_{Tb})(\text{tau}) + (A_{Tc}(T)^2 + B_{Tc}(T) + C_{Tc})$$

wherein:

T is the measured temperature;

tau is the coefficient of the exponential decay curve; and $A_{Ta}$, $B_{Ta}$, $C_{Ta}$, $A_{Tb}$, $B_{Tb}$, $C_{Tb}$, $A_{Tc}$, $B_{Tc}$, and $C_{Tc}$ are previously determined coefficients that are specific to the luminescent compound being examined and that describes the intensity of the luminescent compound as a function of oxygen concentration and temperature. Methods of determining the coefficients are discussed in greater detail in Havens et al. The use of the above equation may permit measurement of oxygen concentration within a sealed package over a wide temperature range.

As shown in FIG. 1, the apparatus may include one or more temperature sensors that are used to measure a temperature that is indicative of the interior of the package, the luminescent compound, or both. In one embodiment, the temperature may be measured by measuring the temperature of the lidstock. Accurately measuring the temperature of the lidstock 42, and hence, the interior space of the container may help to improve the accuracy of the oxygen concentration measurement. From the equation above, it can be seen that the oxygen concentration is a function of temperature. As a result, any error associated with determining the temperature may introduce error into the calculation of oxygen concentration. The Applicants have discovered that limiting heat from the surrounding environment and from the electronics of the apparatus may help improve the accuracy of the calculated oxygen concentration.

To help improve the accuracy of the temperature measurement the apparatus may include an insulating member 28 that is disposed between the housing 26 and an outer surface 46 of the lidstock 42. The insulating member may help thermally isolate the lidstock 42 from the housing 26. In one embodiment one or more temperature sensors 29 are disposed adjacent to the insulating member 28 so that the temperature sensors are also thermally isolated from the housing. The insulating member may also help thermally isolate the temperature sensors from the surrounding environment. The insulating member may comprise any suitable material that can be used to thermally isolate the temperature sensors. Suitable material may include thermoplastic or thermoset polymeric materials.

In some embodiments, the device may include one or more temperature sensors that may be used to determine the outer temperature of the lidstock, and hence, the interior temperature of the container. In some embodiments, the temperature sensor may be capable of accurately measuring the temperature of the package being evaluated within about ±0.1° C. In one embodiment, the temperature sensor may comprise a resistance temperature detector (RTD) that may be positioned in direct contact with an outer surface 46 of the lidstock. In embodiments where the temperature sensor comprises an RTD or similar sensor, an accurate temperature measurement can be obtained by positioning the temperature sensor in contact with the lidstock.

Luminescent compounds that may be used in the practice of the invention include compounds whose molecules are able to be promoted to an excited state by absorbing a photon and then may relax to the ground state by emitting a photon, and wherein such an emission is quenchable by oxygen. In some embodiments, suitable luminescent compounds may include compounds that undergo fluorescence and/or phosphorescence transitions that are capable of being quenched by oxygen. In one embodiment, the luminescent compound comprises a phosphorescent compound that is oxygen quenchable.

Each luminescent compound is typically excited at a specific wavelength that may be different than the wavelengths at which other luminescent compounds are excited. Additionally, the excited luminescent compound may emit light at a wavelength that may be specific to that luminescent compound. As discussed in greater detail below, the device for exciting the luminescent compound and measuring the resulting intensity data may be configured to output light that includes light having a wavelength that is specific to the luminescent compound that is being examined. In some embodiments, the device may be configured to recall information for a plurality of luminescent compounds so that the device may be used in conjunction with one or more luminescent compounds to determine the oxygen concentration within a sealed container.

Suitable luminescent compounds may include porphyrins, meaning those compounds that contain the porphyrin ring structure (Monograph No. 7468, Tenth Edition of The Merck Index, Merck & Company, Inc., Rahway, N.J., 1983), chlorins, bacteriochlorins, and isobacteriochlorins. The porphyrin ring structure gives rise to intense optical absorption and emission in the wavelength range of interest. The wavelengths for absorption and emission can be shifted by various chemical modifications to the porphyrin ring structure. In addition, the emission lifetimes may be strongly dependent on any metal incorporated into the center of the ring. Suitable porphyrins that may be used include metal porphyrins such as tetra(pentafluorophenyl)porphyrin (TFPP), octaethylporphyrin (OEP), tetraphenylporphyrin (TPP), and tetrabenzporphyrin (TBP) compounds. In one embodiments, suitable metals may include second and third transition row metals with electron configurations $d_6$ or $d_8$, including Ru(II), Rh(III), Pd(II), Os(II), Ir(III), Pt(II), and Au(III). Some other metalloporphyrins that may also be suitable, include for example, Hf(IV) octaethylporphyrin. In one embodiment, Pd(II) and Pt(II) complexes of tetra(pentafluorophenyl)porphyrin (TFPP), octaethylporphyrin (OEP), tetraphenylporphyrin (TPP), and tetrabenzporphyrin (TBP) may be particularly useful. In one embodiment, the luminescent compound comprises a metal porphyrin that undergoes a phosphorescent transition.

In some embodiments, the luminescent compound is disposed adjacent to an inner surface of the lidstock. The lidstock may comprise a material that is substantially transparent to the desired excitation light and the light emitted by the excited luminescent compound. In the illustrated embodiment, the lidstock permits the transmission of excitation light and luminescent light. In some embodiments, the lidstock may comprise a film, laminate, web, sheet, or similar structure. The use of a luminescent compound within the package permits determination of the oxygen concentration without a need to physically sample the atmosphere within the container. As a result, the method may be used to determine the oxygen concentration in a sealed container without the having to penetrate or damage the sealed package. Although the invention is generally discussed in terms of applying a luminescent compound to a lidstock, it should be recognized that the term lidstock may also include any transparent packaging medium in which an oxygen sensitive product may be disposed. Such other packaging medium may include, but are not limited to, pouches, bags, containers having a transparent window, and the like. In one embodiment, the package may comprise a bag-like pouch that has been vacuum packaged.

The luminescent compound may be in the form of a label that has been adhered to an inner surface of the lidstock. In one embodiment, the luminescent compound may be disposed in a carrier matrix, such as a polymer. The polymer matrix may be adherable to an interior surface of a sealed package (see briefly FIG. 1, reference number 40). In embodiments where the luminescent compound is disposed within a polymeric matrix, the polymer material should have sufficient permeability so that oxygen may diffuse through the polymeric material and collide with the luminescent compound. The luminescent compound can also or alternatively be present in a material, such as a varnish or resin, that is printed or otherwise applied onto an inner surface of lidstock.

In one embodiment, the range of sensitivity for any particular luminescent molecule used in the oxygen quenching-sensitive composition can be adjusted by choice of the carrier matrix and also the amount of any plasticizer that may be dissolved in the matrix. Polyvinyl chloride with variable amounts of plasticizer may provide suitable carrier matrices, as does polymethyl methacrylate without plasticizer. Other suitable oxygen-permeable matrices can comprise cellulose acetate or silicone-polybicarbonate copolymer.

In one embodiment, a luminescent compound is positioned in an interior space of the container. The luminescent compound may be positioned within the container in an orientation that permits collisions between the luminescent compound and any oxygen molecules that may be present within the container. To measure the oxygen concentration, the apparatus, which is capable of exciting the luminescent compound and measuring the emissions of the luminescent compound, is placed in an oxygen-measuring relationship with the luminescent compound. The apparatus may then emit light, referred to as "excitation light", that is capable of exciting the luminescent compound. A detector within the apparatus measures luminescent intensity of the excited compound as a function of time. From the measured intensity data, the apparatus performs a series of mathematical operations using one or more algorithms to determine the concentration of oxygen within the container.

In another embodiment, the invention includes a method of measuring oxygen concentration at various points throughout the packaging and distribution system. In one embodiment, the method provides a means of assuring the oxygen concentration, and hence the quality of the packaged product throughout various points in the distribution system.

After the product has been placed into the package, and the package has been sealed, the oxygen concentration within the package may be verified with the apparatus. In one embodiment, the oxygen concentration of the sealed package is measured to verify that the oxygen concentration is above or below a predetermined threshold. In some cases, it may be desirable to permit the passage of some time before measuring the oxygen concentration so that a change in oxygen concentration may be observable. In packages having a high or low oxygen concentration, a change in oxygen concentration may indicate that the package has a defective seal or that the package materials themselves do not have the desired oxygen barrier properties. In applications where an oxygen scavenging compound has been incorporated into the package, the change in oxygen concentration may be used to determine if the scavenger is performing properly. Additionally, in other embodiments, successive measurements may be taken to determine the rate of oxygen scavenging.

Figure 2:
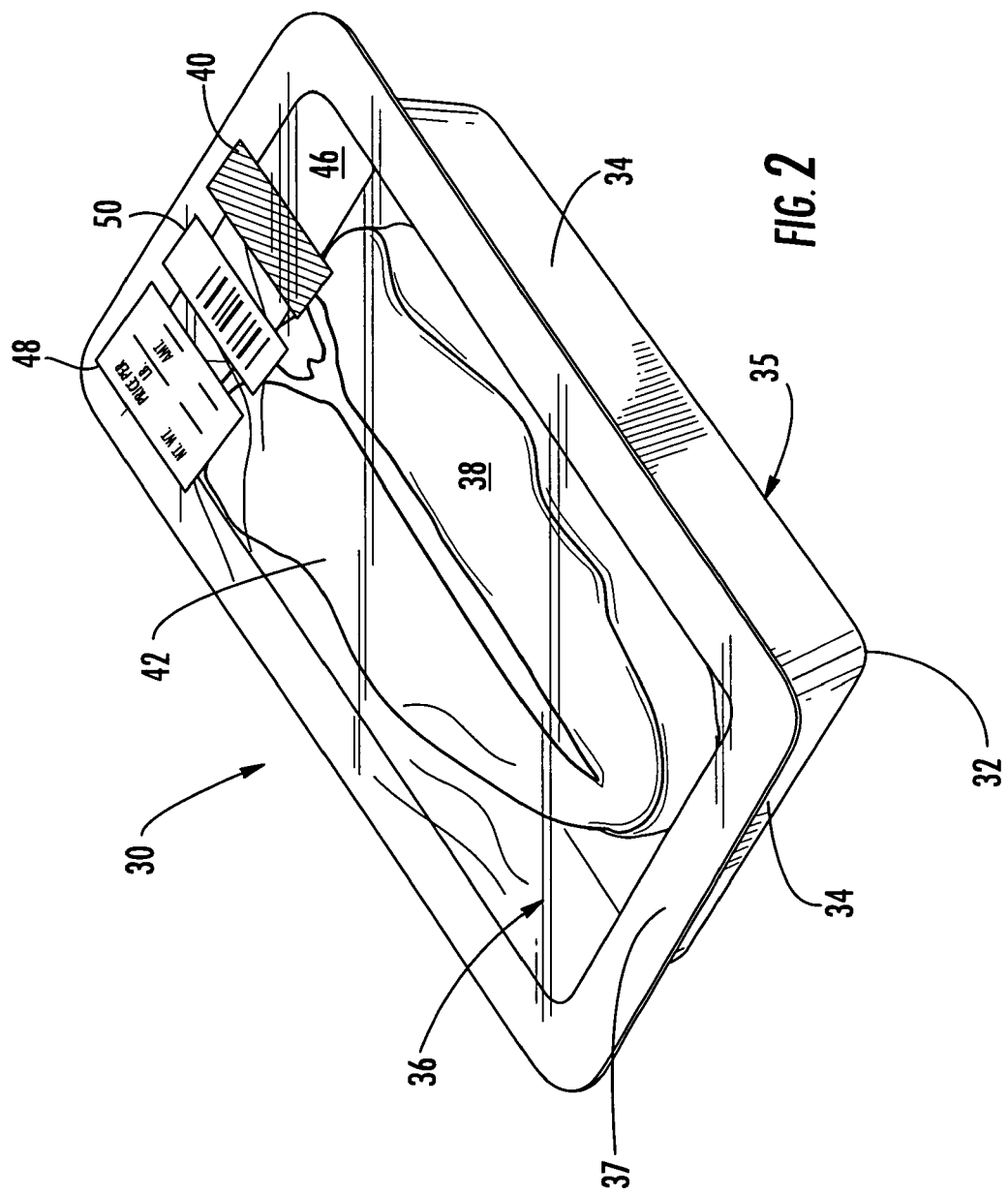
FIG. 2 is a perspective view of a sealed package having a luminescent compound attached to an inner surface of the lidstock.

With reference to FIG. 2, a sealed package 30 is illustrated in which a luminescent compound 40 has been attached to an inner surface of the lidstock 42. In one embodiment, the sealed package 30 may include printed indicia 48 that are attached to, or printed on a surface of the sealed package. Here, the printed indicia 48 are depicted as being on a label that is attached to the outer surface 46 of the lidstock 42. The printed indicia can be used to convey information to a consumer or to one or more persons along the distribution system, such as a distributor, retailer, packager, etc. For example, in one embodiment, the printed indicia includes a predetermined threshold value for a minimum or maximum oxygen concentration in the sealed package. A recipient, such as a retailer, upon receiving the sealed package 30 may measure the oxygen concentration within the sealed package as discussed above. The retailer may then compare the measured oxygen concentration to that on the printed indicia. If the oxygen concentration is below or above the predetermined threshold the retailer may reject the sealed package or take other action as discussed in greater detail below.

In some embodiments, the printed indicia may also include information, such as branding, expiration dates, logos, consumer information, directions for use, and the like.

The sealed package may also include an identification code that may be attached to or printed on an exterior surface of the sealed package. FIG. 2 illustrates a representation of an identification code 50 that is attached to the outer surface 46 of the lidstock. The representation of the identification code 50 permits data representing the identification code to be inputted into a data system. The data system may then use the identification code to recall information for the particular item. In some embodiments, the representation of the identification code 50 may be encoded onto the package in the form of, for example, symbolic, alpha, or numeric information embodied in or on a machine- or human-readable identification code, such as a tag or label (e.g., bar coded tag or label), hole pattern, or radio frequency identification ("RFID") transponder attached or printed onto the sealed package 30. In one embodiment, the representation of the identification code 50 may comprise a bar code that is printed onto the package or that is in the form of a label attached to the package. In other embodiments, the identification code may be in the form of a serial number. Other types of codes may include the particular plant/date/shift/etc under which the product was packaged. In one embodiment, the representation of the identification code may be inputted into a data system with a data entry device. Information associated with the identification code may then be recalled by reading or inputting the representation of the identification code into the data system with a data entry device. Data entry devices may include optical scanners, such as a bar code scanner, RFID reader, magnetic strips, keyboards, and the like.

In some embodiments, the identification code and the luminescent compound may be disposed on the same label. In some cases, the identification code is used to convey information specific to the luminescent compound disposed in the package. Such information may include optimal instrumentation for performing the excitation and measurement functions, the previously determined coefficients for the luminescent compound, one or more algorithms and operational steps for calculating the oxygen concentration, and the like.

Information associated with a particular package may include both product-specific information and item-specific information. Product-specific information may include data for a class of items and typically does not include information about a particular item or product. For example, in one embodiment, the product-specific information may include a predetermined threshold value for a minimum or maximum oxygen concentration for the class of packaging or for a class of product disposed in the sealed package. One or more individuals along the distribution system may use the representation of the identification code to recall the predetermined minimum or maximum oxygen concentration in the sealed package so that it can be compared with the measured oxygen concentration of the sealed package.

Item-specific information on the other hand, may include data that is specific to a particular item such as serial numbers, weight, expiration dates, and the like. In the context of meat packaging, item-specific information may include data that permits traceability of a meat product back to its source. Such data may include, for example, source animal, type of cut, weight, date slaughtered, date packaged, age of the animal, etc. In one embodiment, the item-specific information may include a predetermined minimum or maximum oxygen concentration for the specific package being examined. In some embodiments, the item-specific information may be used to trace the sealed package to the plant in which it was packaged. The item-specific information may also be used to trace the sealed package to a particular time, shift, individual, etc that packaged the particular product. This information may be useful in determining if the failure of the package i.e., oxygen concentration exceeding a maximum or minimum value) may be limited to the specific sealed package or may extend to a plurality of such sealed packages.

In one embodiment, each sealed package may have its own unique identification code that may be used to recall information that is specific to the package being examined. In some embodiments, the unique identification code may be used to recall information that may be unique to the specific item. As discussed in greater detail below, information specific to a particular item may be associated with a unique identification code in the data system. Inputting the unique identification code into the data system may permit an operator to recall and view information specific to the item. In some embodiments, the recalled information may be used to trace or track the history and origin of an item.

The unique identification code may also be used to store information in a data system that is unique to the item. For example, at various points throughout the distribution system, one or more individuals may be able to associate the measured oxygen concentration with the unique identification code in a data system. The stored information can be recalled from the data system by inputting or reading the unique identification code into the system. As a result, the unique identification code may permit the tracing the quality of a product in a sealed package along the distribution system. If a measured oxygen concentration exceeds a maximum or minimum value, the unique identification code may be used to recall stored information relating to that particular package. The recalled information may help in determining at what point the failure (i.e., oxygen concentration exceeding a maximum or minimum value) may have occurred and may also help in making a determination as to the ultimate effects of the failure on the product.

In one embodiment, the identification code may comprise an RFID tag that is attached to the sealed package. In some embodiments, information such as the predetermined minimum or maximum oxygen concentration for the specific package may be recalled from the RFID tag. In other embodiments, the measured oxygen concentration may be written onto the RFID tag so that it can be recalled and/or evaluated at a later time.

From the foregoing discussion it should be evident that the method of measuring oxygen concentration within a sealed package may permit the oxygen concentration to be tracked and recalled throughout the distribution system. As a result, the method may help verify and provide assurance of the quality of the packaged product. In some cases, the method may also be useful in locating and recalling products that may have defective packaging or seals. In addition, the method may also permit the evaluation of stored data to help determine where and/or why a failure in the sealed package may have occurred. Storing oxygen concentrations in a database may also inform the packager/supplier on whether the sealed package arrived at its final destination in a satisfactory state, and may also provide assurances to the end customer, such as a retailer, that the desired level of oxygen concentration was maintained during storage and shipment.

As discussed above, the representation of the identification code may be used in conjunction with a data system that permits information associated with the identification code to be stored and recalled. In one embodiment, the data system may comprise any type of computer system that is capable of storing and retrieving information that is associated with an identification code. The data system may comprise a processor and an associated storage medium from which information associated with an identification code may be recalled. In another embodiment, the data system may comprise one or more computer terminals, such as a personal computer, that may be in communication with one or more storage mediums, for example, a database. In some embodiments, the data system may comprise a centralized computer system that is in communication with one or more data entry devices. In other embodiments, the data system may include one or more storage mediums, such as a database, or a centralized computer or network system. All or parts of the data system may be internal or external to the various points in the distribution system where information regarding the oxygen concentration may be recalled or uploaded to the data system.

Figure 3:
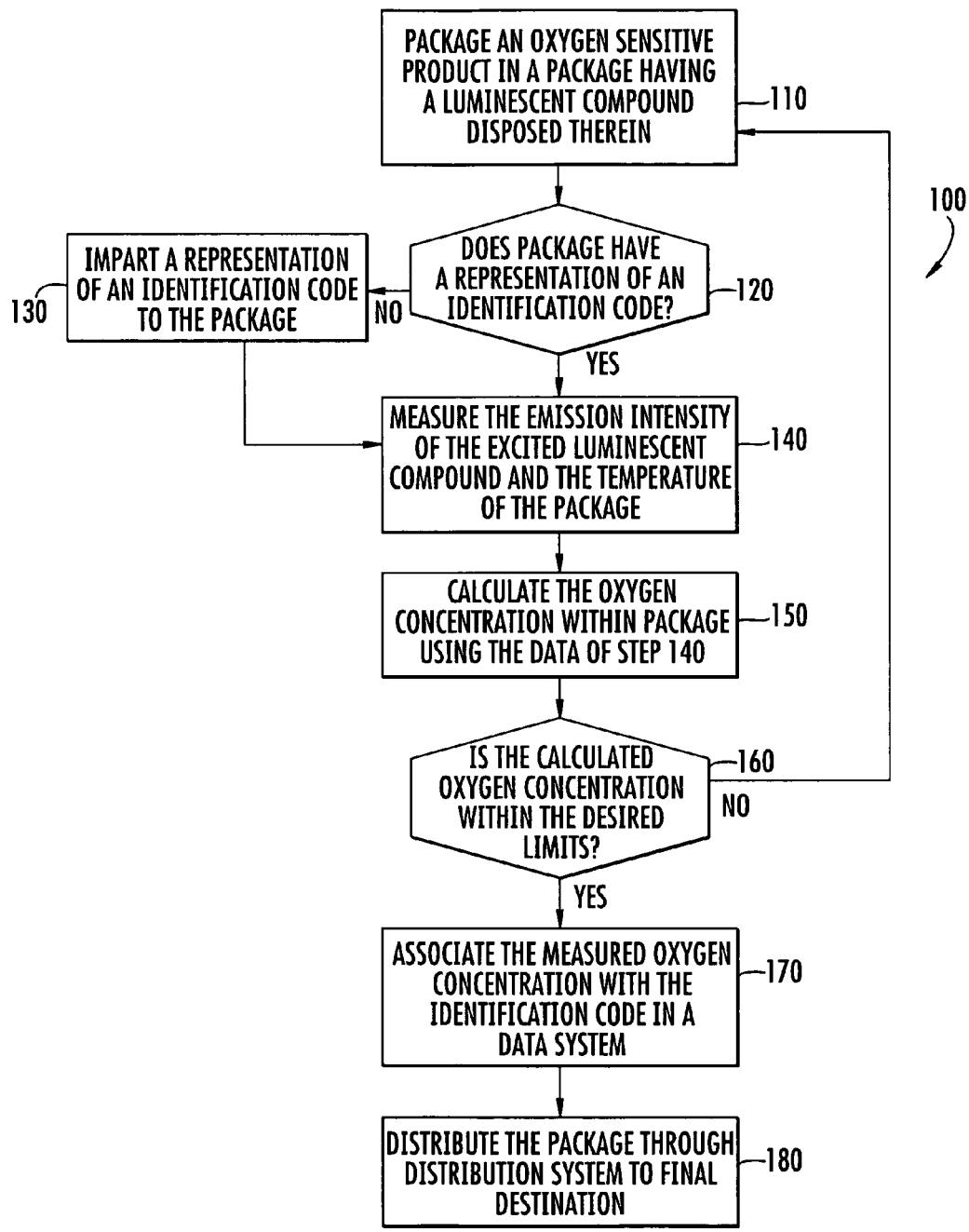
FIG. 3 is a block diagram depicting a method of measuring temperature at a point of packaging.

With reference to FIG. 3, an exemplary method of monitoring the oxygen concentration of sealed package is illustrated and broadly designated as reference number 100. The method 100 provides a rapid means for ensuring that a packaged product has not been exposed to an oxygen concentration exceeding a maximum or minimum value.

As shown in FIG. 3, at step 110 an oxygen sensitive product is packaged and sealed in a package having barrier properties. The sealed package includes a luminescent compound disposed in an oxygen quenching position and in a position that permits an apparatus for measuring oxygen concentration to be placed in an oxygen-measuring relationship with the package (see briefly FIG. 1, reference number 10). In step 120 a packager determines whether the sealed package includes an identification code. If the package does not have an identification code, one may be imparted to it at step 130. In some embodiments, the data system may be capable of generating an identification code.

In the context of the invention, imparting the representation of an identification code may include attaching a label having the representation of the identification code to the package, printing the representation of the identification code onto the package before or after the product has been enclosed in the package, or the use of a package that includes a representation of the identification code that has been previously applied or printed onto the package, or combinations thereof.

Before the sealed package is stored or shipped, it may be desirable to measure its oxygen concentration. At step 140, the temperature of the package and the emission intensity of the excited luminescent compound are measured. The resulting exponential decay curve and the measured temperature are then used to calculate the oxygen concentration within the package at step 150. At step 160 the calculated oxygen concentration is then compared to the desired limits for oxygen concentration within the sealed package. At step 170 the calculated oxygen concentration is within the desired limits, the measured data is associated with the identification code and stored in a data system. The information can then be recalled by inputting the identification code into the data system. The sealed package may then be distributed to a final destination at step 180. In the event the sealed package has an unacceptable oxygen concentration, the product may be discarded or repackaged depending upon its condition. Determining if the package is leaking or that the oxygen concentration is not within the desired limits before the sealed package has been shipped may reduce the possibility of shipping defective or spoiled products to a customer, and may also improve the quality of products associated with the packager/manufacturer. Additionally, locating a leaking or defective package may permit the product to be repackaged. As a result, costs associated with defective or spoiled products may be reduced.

With reference to FIG. 4, a method of monitoring the oxygen concentration within a sealed package is illustrated. The illustrated method is in accordance with method 100 (see FIG. 3), and further comprises additional steps for handling the sealed package at the completion of step 180.

Upon reaching the final destination or some other location along the distribution system, the oxygen concentration can be reevaluated to ensure that it is within the desired limits. At this point, an individual in the distribution system may input the identification code into the data system by reading or scanning a representation of the identification code at step 190. The representation of the identification code may be used to recall information for the sealed package at step 200. As discussed above, the information may include the desired limits for the oxygen concentration. The information may also include operational parameters, algorithms, and the previously determined coefficients for measuring and calculating the oxygen concentration within the sealed package. In some embodiments, such information may be pre-programmed in the apparatus, be readily known or available to the individual performing the analysis, or be printed onto an exterior surface of the sealed package.

At steps 210 and 220, the temperature and emission intensity data may be measured and the oxygen concentration may be calculated as described above. At step 220 the calculated oxygen concentration is then compared to the desired limits for oxygen concentration for the sealed package. If the oxygen concentration is outside the desired limits, the sealed package may be accepted or rejected by the recipient at step 240. If the oxygen concentration is within the desired limits, the sealed package may be accepted by the recipient at step 250. At step 260 the calculated oxygen concentration may be associated with the identification code and stored in a data system. The stored information can then be recalled by inputting the identification code into the data system.

In one embodiment, sealed packages having an acceptable oxygen concentration (i.e., oxygen concentration does not exceed a maximum or minimum value) can be processed in the normal course of business at step 250. The normal course of business refers to the manner in which acceptable packages would normally be treated or handled. For instance, it could refer to continued storage of the packages, shipment of the packages, sale of the packages, or acceptance of the packages.

If the measured oxygen concentration at step 230 indicates that the oxygen concentration has exceeded a maximum or minimum value, the sealed package can be processed as rejected at step 240. There are a variety of different actions that can be taken with respect to rejected packages. For instance, the rejected packages can be returned to the point of origination, such as a supplier, the packages can be held for a subsequent investigation, they could be sold at a discounted price, positioned so as to receive expedited sale or delivery and/or extra cold storage, or the packages could be disposed or discarded.

As discussed above, the method of measuring the oxygen concentration may be used to determine the oxygen concentration in a wide variety of packaging applications without having to sample the atmosphere within the package. In one embodiment, the method may be used to measure the oxygen concentration in low and high oxygen packaging environments, including vacuum packaging and modified atmosphere packaging. MAP involves the modification of the head space gas in a package in order to prolong the shelf life of the product it contains. In some MAP applications, the headspace may have substantially no oxygen. In other MAP applications, the headspace may have a predefined oxygen concentration. The success of MAP generally depends on the ability to control the concentration of oxygen within the package. In vacuum packaging, the atmosphere may be substantially removed so that the package environment is substantially free of oxygen.

For example, in MAP applications for meat products, the raw meat may be packaged in a low level oxygen ($O_2$) environment. Packaging systems having low levels of oxygen are desirable because the fresh quality of meat can generally be preserved longer under anaerobic conditions than under aerobic conditions. Typically, some low oxygen packaging environments may provide an atmosphere that helps prevent or inhibit excessive metmyoglobin (brown) formation in red meat products. Maintaining low levels of oxygen minimizes the growth and multiplication of aerobic bacteria.

One example of a modified atmosphere environment is a mixture of gases consisting of about 30 percent carbon dioxide ($CO_2$) and about 70 percent nitrogen ($N_2$). Other modified atmosphere environments may include a mixture of gases that comprise from about 0.1 to 5.0 vol. % carbon monoxide. In some embodiments, the low oxygen atmosphere may include at least 0.1 vol. % carbon monoxide. In red meat products, the carbon monoxide in the package reacts with myoglobin to form carboxymyoglobin to produce a cherry red color, which consumers may find desirable. The modified atmosphere packaging having a low oxygen atmosphere may enable the food product to be shipped and stored for a relatively longer period of time. In one embodiment, the method may be used to determine the oxygen concentration in a sealed package in which a food item such as a retail cut of raw meat may be disposed in the package. In some embodiments, the raw meat may be any animal protein, including beef, pork, veal, lamb, chicken, turkey, venison, fish, etc.

Examples of low oxygen environments include, but are not limited, to about 40 vol. % carbon dioxide and about 90 vol. % nitrogen. In some embodiments, the low oxygen environment may include up to about 5% vol. carbon monoxide. It is contemplated that other combinations of carbon dioxide and nitrogen may be used. For example, the low oxygen environment may include from about 40 to about 80 vol. % nitrogen and from about 20 to about 60 vol. % carbon dioxide. The low oxygen environment may include from about 0.1 vol. % to about 3.0 vol. % carbon monoxide. In one embodiment, the modified atmosphere may comprise about 0.4% vol. carbon monoxide, about 30% vol. carbon dioxide, with nitrogen comprising the remaining balance. In some embodiments, the modified atmosphere may include additional gases in the mixture, for example, one or more noble gases.

A modified atmosphere packaging comprising carbon monoxide is believed to protect the pigment myoglobin on or near the surface of the meat during the oxygen reduction phase, allowing the meat to have a desired display color (i.e., a full bloom). While not being bound by theory, it is believed that the low level of carbon monoxide in the gas mixture forms carboxymyoglobin (red) and protects the myoglobin from reaching the metmyoglobin (brown) or deoxymyoglobin (purple-red) state during storage and/or display. Before converting to carboxymyoglobin, a surface of the meat may be at least partially oxygenated (oxymyoglobin). By converting to carboxymyoglobin on at least the surface of the meat, the myoglobin is protected during the oxygen reduction period when it is vulnerable to the formation of metmyoglobin. This protection is especially important from about 2 vol. % to about 500 or 1000 ppm oxygen when metmyoglobin forms rapidly. The myoglobin pigment of the meat is also protected by the mixture of gases used in the present invention even when the meat is stored in a foam tray that may slowly diffuse oxygen when packaged in a low oxygen package.

Referring back to FIG. 2, an exemplary package for use in low oxygen packaging applications may includes product support member 32 having a cavity 36 or interior space formed therein and a product 38 disposed within the cavity. Support member 32 may be in the form of a tray having side walls 34 and a base 35 which define the cavity 36, and further may include a peripheral flange 37 extending outwardly from the cavity. Lidstock 42 forms a lid on the package 30 and encloses the product 38 within cavity 36 by being heat-welded or otherwise bonded to flange 37. In some embodiments, the lidstock 42 may be attached to the support member using other means including adhesive bonding, ultrasonic bonding, etc. In one embodiment, the package 30 may include a label 48 that may include product information, such as pricing, description, expiration date, etc. Label 48 may be placed on the package at the point of packaging or by the retailer at the point-of-sale.

In some embodiments, the package 30 may also include a representation of an identification code 50, such as a bar code, that is attached to or printed on the package. As discussed above, the identification code may be used to recall and store information relating to the packaged product.

Support member 32 can have any desired configuration or shape, e.g., rectangular, round, oval, etc. Similarly, flange 37 may have any desired shape or design, including a simple, substantially flat design which presents a single sealing surface as shown, or a more elaborate design which presents two or more sealing surfaces, such as the flange configurations disclosed in U.S. Pat. Nos. 5,348,752 and 5,439,132, the disclosures of which are hereby incorporated herein by reference.

Suitable materials from which support member 32 can be formed may include, without limitation, polyvinyl chloride, polyethylene terephthalate, polystyrene, polyolefins such as high density polyethylene or polypropylene, paper pulp, nylon, polyurethane, and combinations thereof. The support member may be foamed or non-foamed (e.g., solid or semi-solid) as desired. Support member 32 may have oxygen transmission barrier attributes, particularly when product 38 is an oxygen-sensitive food product. When such oxygen-sensitive products are to be packaged in a modified atmosphere environment to extend either bloom-color life or shelf-life, support member 32 may have a thickness and composition sufficient to provide an oxygen transmission rate of no more than about any of the following values: 1000, 500, 150, 100, 50, 45, 40, 35, 30, 25, 20, 15, 10, and 5 cubic centimeters (at standard temperature and pressure) per square meter per day per 1 atmosphere of oxygen pressure differential measured at 0% relative humidity and 23° C. Unless otherwise stated all references to oxygen transmission rate are measured according to ASTM D-3985.

To achieve oxygen barrier attributes, support member 32 may comprise one or more oxygen barrier components, such as a substantially oxygen impermeable film or laminate in order to provide oxygen barrier attributes to the support member. Such barrier components may be incorporated within structural sections or aspects of the support member—or optionally incorporated in an inner surface layer or film (not shown) laminated or otherwise bonded to form the inside surface of the support member, as described in U.S. Pat. Nos. 4,847,148 and 4,935,089, and in U.S. Ser. No. 08/326,176, filed Oct. 19, 1994 and entitled "Film/Substrate Composite Material" (published as EP 707 955 A1 on Apr. 24, 1996), each of which is incorporated herein in its entirety by reference.

In addition to (or as an alternative to) providing oxygen barrier attributes, the inner surface layer or film of the support member may enhance the sealability of the lidstock 42 to the support member 32. In heat sealing the lidstock to the support member 32, the surface layer of the support member may contact and meld with an inner surface of the lidstock 42 to form a heat seal. To facilitate a strong heat seal, the surface layer of the support member may comprise one or more thermoplastics that are compatible with the thermoplastic composition of the lidstock 42.

The height of the product 38 within the tray may be low profile or high profile. "Low profile" refers to packages wherein the product has a maximum height which is below the maximum height of support member 32, i.e., the level at which flange 37 is located. "High profile" products may also be packaged in accordance with the present invention, i.e., those having a maximum height which is above the level at which flange 37 is located so that the portion of the product which extends above the level of flange 37 will be in contact with lidstock 42.

In one alternative embodiment, the lidstock 42 may comprise a single or multilayer film or laminate which is substantially impermeable to oxygen. In one embodiment, the lidstock may comprise a laminate comprising two or more films. The film(s) may be monolayer, two-layer, or have three or more layers. The lidstock 42 may be laminated to the support member (e.g., a tray) to form sealed package 30 in which a food product 38 may be enclosed.

In one alternative embodiment, the lidstock may comprise a film having one or more barrier layers, which incorporate one or more components ("barrier components") that markedly decrease the oxygen transmission rate through the layer and thus the film incorporating such layer. Accordingly, the barrier layer of the film that is utilized in a lidstock incorporated in a package may either help to exclude oxygen from the interior of the package—or to maintain a modified atmosphere within the package. In one embodiment, the lidstock may have a thickness and composition sufficient to provide an oxygen transmission rate of no more than about any of the following values: 1000, 500, 150, 100, 50, 45, 40, 35, 30, 25, 20, 15, 10, and 5 cubic centimeters (at standard temperature and pressure) per square meter per day per 1 atmosphere of oxygen pressure differential measured at 0% relative humidity and 23° C. In one embodiment, the package comprises a barrier layer having an oxygen transmission rate no greater than 10 cc at STP/m$^2$/24 hr/atm.

Useful barrier components may include: ethylene/vinyl alcohol copolymer ("EVOH"), polyvinyl alcohol ("PVOH"), vinylidene chloride polymers ("PVdC"), polyalkylene carbonate, polyester (e.g., PET, PEN), polyacrylonitrile ("PAN"), and polyamide. In some embodiments the lidstock may also include one or more thermoplastic polymers including polyolefins, polystyrenes, polyurethanes, polyvinyl chlorides, polyesters, and ionomers provided that the desired barrier properties of the lidstock may be maintained.

Suitable polyolefins for use in the lidstock may include LLDPE, low density polyethylene, high density polyethylene, metallocene catalyzed polyethylene, polypropylene, and oriented polypropylene, ethylene homo- and co-polymers and propylene homo- and co-polymers. Ethylene homopolymers include high density polyethylene ("HDPE") and low density polyethylene ("LDPE"). Ethylene copolymers include ethylene/alpha-olefin copolymers ("EAOs"), ethylene/unsaturated ester copolymers, and ethylene/(meth) acrylic acid. ("Copolymer" as used in this application means a polymer derived from two or more types of monomers, and includes terpolymers, etc.).

EAOs are copolymers of ethylene and one or more alpha-olefins, the copolymer having ethylene as the majority mole-percentage content. In some embodiments, the comonomer includes one or more $C_3$-$C_{20}$ alpha-olefins, such as one or more $C_4$-$C_{12}$ alpha-olefins, e.g. one or more $C_4$-$C_8$ alpha-olefins. Particularly useful alpha-olefins include 1-butene, 1-hexene, 1-octene, and mixtures thereof.

EAOs include one or more of the following: 1) medium density polyethylene ("MDPE"), for example having a density of from 0.93 to 0.94 g/cm$^3$; 2) linear medium density polyethylene ("LMDPE"), for example having a density of from 0.926 to 0.94 g/cm$^3$; 3) linear low density polyethylene ("LLDPE"), for example having a density of from 0.915 to 0.930 g/cm3; 4) very-low or ultra-low density polyethylene ("VLDPE" and "ULDPE"), for example having density below 0.915 g/cm$^3$; and 5) homogeneous EAOs. Useful EAOs include those having a density of less than about any of the following: 0.925, 0.922, 0.92, 0.917, 0.915, 0.912, 0.91, 0.907, 0.905, 0.903, 0.9, and 0.898 grams/cubic centimeter. Unless otherwise indicated, all densities herein are measured according to ASTM D1505.

The polyethylene polymers may be either heterogeneous or homogeneous. As is known in the art, heterogeneous polymers have a relatively wide variation in molecular weight and composition distribution. Heterogeneous polymers may be prepared with, for example, conventional Ziegler Natta catalysts.

On the other hand, homogeneous polymers are typically prepared using metallocene or other single site-type catalysts. Such single-site catalysts typically have only one type of catalytic site, which is believed to be the basis for the homogeneity of the polymers resulting from the polymerization. Homogeneous polymers are structurally different from heterogeneous polymers in that homogeneous polymers exhibit a relatively even sequencing of comonomers within a chain, a mirroring of sequence distribution in all chains, and a similarity of length of all chains. As a result, homogeneous polymers have relatively narrow molecular weight and composition distributions. Examples of homogeneous polymers include the metallocene-catalyzed linear homogeneous ethylene/alpha-olefin copolymer resins available from the Exxon Chemical Company (Baytown, Tex.) under the EXACT trademark, linear homogeneous ethylene/alpha-olefin copolymer resins available from the Mitsui Petrochemical Corporation under the TAFMER trademark, and long-chain branched, metallocene-catalyzed homogeneous ethylene/alpha-olefin copolymer resins available from the Dow Chemical Company under the AFFINITY trademark.

Another useful ethylene copolymer is ethylene/unsaturated ester copolymer, which is the copolymer of ethylene and one or more unsaturated ester monomers. Useful unsaturated esters include: 1) vinyl esters of aliphatic carboxylic acids, where the esters have from 4 to 12 carbon atoms, and 2) alkyl esters of acrylic or methacrylic acid (collectively, "alkyl (meth)acrylate"), where the esters have from 4 to 12 carbon atoms.

Representative examples of the first ("vinyl ester") group of monomers include vinyl acetate, vinyl propionate, vinyl hexanoate, and vinyl 2-ethylhexanoate. The vinyl ester monomer may have from 4 to 8 carbon atoms, from 4 to 6 carbon atoms, from 4 to 5 carbon atoms, and preferably 4 carbon atoms.

Representative examples of the second ("alkyl(meth)acrylate") group of monomers include methyl acrylate, ethyl acrylate, isobutyl acrylate, n-butyl acrylate, hexyl acrylate, and 2-ethylhexyl acrylate, methyl methacrylate, ethyl methacrylate, isobutyl methacrylate, n-butyl methacrylate, hexyl methacrylate, and 2-ethylhexyl methacrylate. The alkyl (meth)acrylate monomer may have from 4 to 8 carbon atoms, from 4 to 6 carbon atoms, and preferably from 4 to 5 carbon atoms.

The unsaturated ester (i.e., vinyl ester or alkyl(meth)acrylate)comonomer content of the ethylene/unsaturated ester copolymer may range from about 3 to about 18 weight %, and from about 8 to about 12 weight %, based on the weight of the copolymer. Useful ethylene contents of the ethylene/unsaturated ester copolymer may include the following amounts: at least about 82 weight %, at least about 85 weight %, at least about 88 weight %, no greater than about 97 weight %, no greater than about 93 weight %, and no greater than about 92 weight %, based on the weight of the copolymer.

Representative examples of ethylene/unsaturated ester copolymers may include ethylene/methyl acrylate, ethylene/methyl methacrylate, ethylene/ethyl acrylate, ethylene/ethyl methacrylate, ethylene/butyl acrylate, ethylene/2-ethylhexyl methacrylate, and ethylene/vinyl acetate. Another useful ethylene copolymer is ethylene/(meth)acrylic acid, which is the copolymer of ethylene and acrylic acid, methacrylic acid, or both.

Useful propylene copolymer may include propylene/ethylene copolymers ("EPC"), which are copolymers of propylene and ethylene having a majority weight % content of propylene, such as those having an ethylene comonomer content of less than 10%, preferably less than 6%, and more preferably from about 2% to 6% by weight.

Ionomer is a copolymer of ethylene and an ethylenically unsaturated monocarboxylic acid having the carboxylic acid groups partially neutralized by a metal ion, such as sodium or zinc, preferably zinc. Useful ionomers may include those in which sufficient metal ion is present to neutralize from about 15% to about 60% of the acid groups in the ionomer. The carboxylic acid is preferably "(meth)acrylic acid"—which means acrylic acid and/or methacrylic acid. Useful ionomers include those having at least 50 weight % and preferably at least 80 weight % ethylene units. Useful ionomers also include those having from 1 to 20 weight percent acid units. Useful ionomers are available, for example, from Dupont Corporation (Wilmington, Del.) under the SURLYN trademark.

In some embodiments, EVOH may have an ethylene content of between about 20% and 40%, preferably between about 25% and 35%, more preferably about 32% by weight. EVOH may include saponified or hydrolyzed ethylene/vinyl acetate copolymers, such as those having a degree of hydrolysis of at least 50%, preferably of at least 85%.

Vinylidene chloride polymer ("PVdC") refers to a vinylidene chloride-containing polymer or copolymer—that is, a polymer that includes monomer units derived from vinylidene chloride (CH2=CCl2) and also, optionally, monomer units derived from one or more of vinyl chloride, styrene, vinyl acetate, acrylonitrile, and C1-C12 alkyl esters of (meth) acrylic acid (e.g., methyl acrylate, butyl acrylate, methyl methacrylate). As used herein, "(meth)acrylic acid" refers to both acrylic acid and/or methacrylic acid; and "(meth)acrylate" refers to both acrylate and methacrylate. Examples of PVdC include one or more of the following: vinylidene chloride homopolymer, vinylidene chloride/vinyl chloride copolymer ("VDC/VC"), vinylidene chloride/methyl acrylate copolymer, vinylidene chloride/ethyl acrylate copolymer, vinylidene chloride/ethyl methacrylate copolymer, vinylidene chloride/methyl methacrylate copolymer, vinylidene chloride/butyl acrylate copolymer, vinylidene chloride/styrene copolymer, vinylidene chloride/acrylonitrile copolymer, and vinylidene chloride/vinyl acetate copolymer. Useful PVdC may include those having between 75 and 95 weight % vinylidene chloride monomer. Useful PVdC includes that having from about 5 to about 25 weight %, from about 10 to about 22 weight %, and from about 15 to about 20 weight % comonomer with the vinylidene chloride monomer. Useful PVdC includes that having a weight-average molecular weight (Mw) of at least 80,000, such as at least 90,000, at least 100,000, at least 111,000, at least 120,000, at least 150,000, and at least 180,000; and between 80,000 and 180,000, such as between 90,000 and 170,000, between 100,000 and 160,000, between 111,000 and 150,000, and between 120,000 and 140,000. Useful PVdC may also include that having a viscosity-average molecular weight (Mz) of at least 130,000, such as at least 150,000, at least 170,000, at least 200,000, at least 250,000, and at least 300,000; and between 130,000 and 300,000, such as between 150,000 and 270,000, between 170,000 and 250,000, and between 190,000 and 240,000.

A barrier layer that includes PVdC may also include a thermal stabilizer (e.g., a hydrogen chloride scavenger such as epoxidized soybean oil) and a lubricating processing aid (e.g., one or more acrylates).

Useful polyamides may include polyamide 6, polyamide 9, polyamide 10, polyamide 11, polyamide 12, polyamide 66, polyamide 610, polyamide 612, polyamide 61, polyamide 6T, polyamide 69, copolymers made from any of the monomers used to make two or more of the foregoing homopolymers (e.g., copolyamide 6/12, polyamide 12, copolyamide 66/69/61, copolyamide 66/610, copolyamide 6/66, and copolyamide 6/69), and blends of any of the foregoing homo- and/or copolymers. Polyamide copolymers include: (a) copolyamide 6/12 comprising (i) caprolactam mer in an amount of from about 20 to 80 weight percent (preferably 30 to 70 weight percent, more preferably 40 to 60 weight percent), and (ii) laurolactam mer in an amount of from about 80 to 20 weight percent; and (b) copolyamide 66/69/61 comprising 10 to 50 weight percent hexamethylene adipamide mer (preferably from about 20 to 40 weight percent), 10 to 50 weight percent polyamide 69 mer (preferably from about 20 to 40 weight percent), and 10 to 60 weight percent hexamethylene isophthalamide mer (preferably, from about 10 to 40 weight percent).

In some embodiments, the lidstock may also comprise one or more additional layers or films including one or more sealant layers, tie layers, bulk layers, etc. In some embodiments, the lidstock may comprise a trap-printable laminate having barrier properties. Such laminates are discussed in greater detail in U.S. Pat. Nos. 6,627,273 and 6,769,227, the contents of which are hereby incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of verifying the oxygen concentration of a sealed package comprising:
   providing a sealed package defining an interior and having a luminescent compound provided in the interior of the sealed package the luminescent compound having a luminescent emission that is sensitive to quenching by oxygen;
   exposing the luminescent compound to light having a wavelength that is absorbed by the luminescent compound so that the luminescent compound is promoted into an excited state;
   terminating the exposure of the luminescent compound when the luminescent compound achieves a steady state between excitation and luminescence;
   measuring luminescent intensity over a period of time to produce an exponential decay curve;
   calculating the coefficient of the decay curve to determine tau;
   measuring a temperature that is indicative of the temperature of the luminescent compound;

determining the oxygen concentration within the sealed package using the equation:

$$[O_2]=(A_{Ta}(T)^2+B_{Ta}(T)+C_{Ta})(\tau)^2+(A_{Tb}(T)^2+B_{Tb}(T)+C_{Tb})(\tau)+(A_{Tc}(T)^2+B_{Tc}(T)+C_{Tc})$$

wherein:

T is the measured temperature;

tau is the coefficient of the exponential decay curve; and $A_{Ta}$, $B_{Ta}$, $C_{Ta}$, $A_{Tb}$, $B_{Tb}$, $C_{Tb}$, $A_{Tc}$, $B_{Tc}$, and $C_{Tc}$ are previously determined coefficients for the luminescent compound that describes the luminescent intensity of the luminescent compound as a function of oxygen concentration and temperature; and comparing the measured oxygen concentration to a predetermined minimum or maximum to verify that the measured oxygen concentration is within acceptable limits.

2. A method according to claim 1, wherein the coefficient of the decay curve is calculated by calculating the area under the decay curve.

3. A method according to claim 1, wherein the sealed package includes an oxygen sensitive product disposed therein.

4. A method according to claim 1, wherein a meat product is disposed in the interior of the sealed package.

5. A method according to claim 1, wherein the sealed package comprises a low oxygen atmosphere.

6. A method according to claim 5, wherein the low oxygen atmosphere comprises nitrogen, carbon monoxide, carbon dioxide, argon, or a combination thereof and substantially no oxygen.

7. A method according to claim 5, wherein the sealed package comprises a vacuum package or a modified atmosphere package.

8. A method according to claim 1, wherein the sealed package includes a representation of a unique identification number and further comprises the step of inputting the representation of the unique identification code into a data system.

9. A method according to claim 8, further comprising the step of associating the calculated oxygen concentration with the unique identification number in the data system.

10. A method according to claim 9, wherein the representation of the unique identification code is a machine readable code and the step of inputting the unique identification code comprises scanning the machine readable representation of the unique identification code with a data entry device.

11. A method according to claim 1, further comprising imparting a representation of a unique identification code to the sealed package and wherein the unique identification code is associated with information that is unique to the sealed package in a data system.

12. A method according to claim 1, wherein the step of measuring a temperature further comprises contacting an outer surface of the sealed package with a temperature sensor that is thermally isolated from the surrounding environment.

13. A method according to claim 1, wherein the luminescent compound is in the form of a label.

14. A method according to claim 1, wherein the luminescent compound comprises a metal porphyrin.

* * * * *